United States Patent [19]

Schoen, Jr.

[11] Patent Number: 4,701,052
[45] Date of Patent: Oct. 20, 1987

[54] DEW POINT HYGROMETER

[76] Inventor: Oscar W. Schoen, Jr., P.O. Box 408, Organ, N. Mex. 88052-0408

[21] Appl. No.: 737,619

[22] Filed: May 24, 1985

[51] Int. Cl.⁴ ............................................. H04L 25/49
[52] U.S. Cl. ...................................... 356/369; 374/19
[58] Field of Search ..................................... 356/36-38, 356/364, 369, 445, 381, 382; 374/5, 15-20, 28, 30; 340/580-581, 583, 602; 73/335, 336.5

[56] References Cited

U.S. PATENT DOCUMENTS

| | | | |
|---|---|---|---|
| 2,415,776 | 2/1947 | Walton | 374/15 |
| 3,597,084 | 8/1971 | Pagano | 356/37 |
| 3,623,356 | 11/1971 | Bisberg | 374/20 |
| 3,904,293 | 9/1975 | Gee | 356/369 |
| 4,216,669 | 8/1980 | Harding | 374/20 |
| 4,526,011 | 7/1985 | Logan et al. | 340/602 X |

FOREIGN PATENT DOCUMENTS 0015532  1/1985  Japan ................................ 356/369

Primary Examiner—R. A. Rosenberger
Attorney, Agent, or Firm—Saul Elbaum; Alan J. Kennedy; Thomas E. McDonald

[57] ABSTRACT

A hygrometer utilizing condensation at the dew point to determine the water content of a gas. The presence of the condensate is determined using linear polarized light to distinguish the condensate from the metal surface on which it forms. A temperature gradient is established across the surface so that condensate forms on only part of the surface. The portion of the surface covered gives an indication of the temperature of the dew point.

3 Claims, 3 Drawing Figures

4,701,052

DEW POINT HYGROMETER

BACKGROUND OF THE INVENTION

1. Field of the Invention:

This invention relates generally to dew point hygrometers and more particularly to dew point hygrometers using polarized light and a condensation surface with a temperature gradient in the plane of the surface.

2. Description of the Prior Art

It is well known that the dew point of a moisture containing gas is a function of the amount of moisture contained in the gas. The dew point hygrometer makes use of this concept to determine the water content of a gas. Gas is passed over a surface as the surface is cooled until condensation forms on the surface. The temperature of the surface is then measured to determine the dew point temperature of the gas which can be correlated to the moisture content of the gas.

This method has been the most accurate technique for determining moisture content of a gas and is well known. However, prior art devices have determined the presence of condensation by reflecting light off the surface and measuring the relative amounts of diffuse and specular reflection. Without condensation, the polished metal surface produces only a specular reflection. Condensation normally produces a diffuse reflection.

However, under certain circumstances, such as at temperatures below −60° F., the condensation forms as glaze ice on the surface. Glaze ice gives a specular reflection similar to the metal surface, rather than a diffuse reflection. As a result, inaccurate results are produced by this method when glaze ice is formed.

Also, even in the absence of glaze ice, certain inaccuracies in measuring the temperature are encountered. The metal surface is typically cooled from below, resulting in a temperature gradient through the thickness of the metal, normal to the surface. Since the temperature of the metal is measured at a point below the surface, the measured temperature will be slightly different from the temperature at the surface. Further, since it is not possible to detect when condensation is imminent, but only possible to detect it after it has happened, the forming condensation adds a further temperature gradient. Finally, there is a gradient across the thickness dimension of the gas in laminar flow and within the boundary in turbulent flow. The result of this is that the measured temperature is not exactly the temperature of the gas.

SUMMARY OF THE INVENTION

Accordingly, one object of this invention is to provide a novel dew point hygrometer which is accurate and reliable.

Another object of this invention is to provide a new and improved hygrometer which is accurate even when glaze ice is formed.

A further object of this invention is to provide a hygrometer which utilizes polarized light to detect condensation.

A still further object of this invention is to provide a hygrometer having a temperature gradient along and in the plane of the condensation surface.

Another object of this invention is to provide an accurate dew point hygrometer which detects glaze ice using polarized light and which uses a temperature gradient on the condensation surface to better determine the dew point temperature.

Briefly these and other objects of the invention are accomplished by providing a polarized light source for detecting the condensation in order to differentiate between condensation, including glaze ice, and the metal surface. Detectors of specular and diffuse reflections detect the polarization of the light reflected. The condensation surface has a temperature gradient along its length so that condensation occurs only on that part of the surface with a temperature below the dew point temperature.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
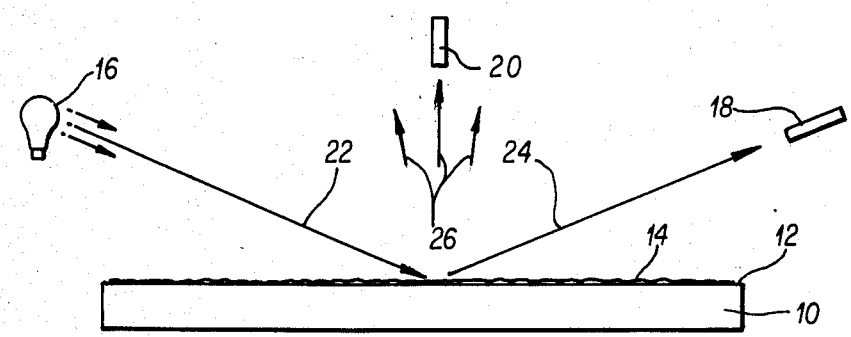
FIG. 1 is a cross sectional view of the prior art device.

Referring now to the drawings, wherein like reference numerals designate identical or corresponding parts throughout the several views, and more particularly to FIG. 1 thereof, where a prior art dew point hygrometer is shown as including a metal piece 10 having a polished metal surface 12 for receiving condensation. Gas is passed over the surface as the surface is cooled from below to cause condensation 14 to form on the surface. The temperature at which this occurs depends on the moisture content of the gas. By determining the temperature when condensation occurs, the moisture content is determined. In order to determine when condensation forms, a light source 16 is used to project a light beam 22 onto the surface. If no condensation is present, the reflective surface reflects the beam 22 specularly as beam 24, which is detected by detector 18. If condensation is present, the light is reflected at least partially diffusely in beams 26. The amount of diffuse reflection depends on the thickness of the condensation. Diffuse reflections are detected by detector 20. Detectors 18 and 20 may be connected in a bridge circuit to control the amount of cooling applied to the surface 12 so that only a thin layer of condensation is formed.

Figure 2:
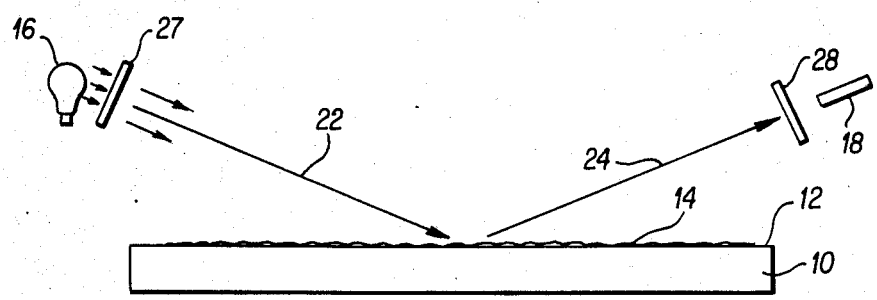
FIG. 2 is a cross sectional view of the present invention.

FIG. 2 shows the improved hygrometer of the present invention as including the same surface on which condensation forms and a similar arrangement of light source and detector 18 as shown in FIG. 1. In addition, however, the present invention includes polarizer 27 which causes input beam 22 to be linearly polarized and analyzer 28 for determining if the specularly reflected beam 24 is linearly or elliptically polarized.

The purpose of the polarized light is to distinguish between the bare metal surface and specularly reflecting condensed glaze ice. It is known that for all metals, linearly polarized input light is not reflected as linearly polarized light except when the direction of polarization is either in the plane of incidence or perpendicular to it. When the direction of polarization is at any other angle, the reflected beam contains electric field components with a change in phase from the incident beam, producing an elliptical polarization of the reflected beam. If the same input beam were directed to a dielectric surface at an angle equal to Brewster's angle, the reflected beam would be linearly polarized in a direction perpendicular to the plane of incidence.

Thus, the presence of condensation on the metal may be determined by analyzing the polarization of the reflected beam using analyzer 28. This analyzer is a polarizer similar to polarizer 27. The analyzer is adjusted by rotating it until it completely blocks the transmission of the reflected beam when there is condensation on the metal surface. Since the beam reflected from the dielectric condensation is essentially composed only of a component perpendicular to the plane of incidence, the analyzer is in effect used to block this component. When the beam is reflected from bare metal the beam is composed of components both perpendicular to and parallel to the plane of incidence. The analyzer stops only the perpendicular component and transmits the parallel component. Thus, detector 18 will receive light only when the metal is bare. When condensation forms, the light disappears. The light may be used to control the cooling rate of the metal in the same manner as detector 20 in the prior art device. Thus, the use of polarized light allows the hygrometer to detect any kind of condensation, even glaze ice.

Figure 3:
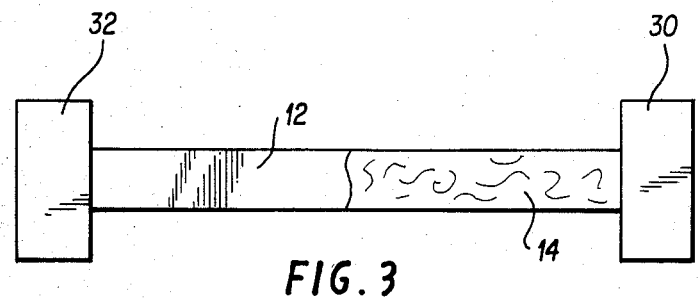
FIG. 3 is a top view of the present invention.

FIG. 3 shows another feature of the present invention which results in more accurate results. As pointed out above, by cooling the metal from below, temperature gradients are formed in the thickness of the metal which make an accurate determination of the gas temperature impossible. The present invention uses the temperature gradient to help determine the temperature rather than allowing it to act as a source of error.

As shown in FIG. 3, the condensation surface 12 may be used to form condensation 14 from a gas sample. A heat sink or cooling device 30 is placed at one end of the surface 12 in order to cool the metal, while a heat source 32 is placed at the opposite end of the surface. The heat sink and source have a temperature difference between them which can be measured and controlled. Heat flowing from the source to the sink sets up a temperature gradient along the length of the surface. By measuring the temperatures of the heat sink and heat source, the temperatures at intervals along the surface can be determined. If condensation forms only on part of the surface, such as shown in FIG. 3, the temperature of the surface at the demarcation line between the condensation and bare surface is the dew point temperature of the gas. The dew point temperature is easily calculated by multiplying the distance from the demarcation line to a known temperature point, in this case the temperature of the heat sink, by the temperature gradient, and adding the result to that known temperature. If the known temperature point is the heat source the result is subtracted from that temperature. The gradient can be established by dividing the temperature difference between two points by the distance between the same points.

If the temperature of the heat sink and source is held constant, the demarcation line will move toward the warm end of the surface as the moisture content of the gas increases. Alternatively, by changing the temperature of the end points, the demarcation line may be maintained at a predetermined location on the surface. In either case, the dew point temperature may be measured as indicated above. Thus, the temperature gradient introduces no error into the measurement, but rather becomes an indication for the measurement, allowing more accurate results.

The surface shown in FIG. 3 may be either a planar surface or may be a cylindrical surface with the axis of the cylinder extending between the source and sink.

The two features of the invention, the polarized light source and the temperature gradient measuring device, are preferably used together for the most accurate hygrometer device.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A dew point hygrometer, comprising:
    a specular metal surface;
    a heat sink for cooling said metal surface;
    a polarized light source for providing linearly polarized light incident on said metal surface;
    an analyzer for receiving light reflected from said metal surface and transmitting only light with certain predetermined polarization;
    a light detector for producing an output when light is transmitted through said analyzer;
    wherein condensation forming on said cooled metal surface causes said reflected light to change polarization and be blocked by said analyzer, thus causing said light detector to produce no output.

2. The hygrometer according to claim 1 wherein said analyzer is a polarizer.

3. The dew point hygrometer according to claim 1, wherein said metal surface is planar.

* * * * *